United States Patent [19]

Dungill

[11] Patent Number: 4,515,563

[45] Date of Patent: May 7, 1985

[54] AMALGAM CARRIER

[76] Inventor: Kenneth F. Dungill, 2049 Hall St., SE., East Grand Rapids, Mich. 49506

[21] Appl. No.: 468,884

[22] Filed: Feb. 23, 1983

[51] Int. Cl.³ .............................................. A61C 5/04
[52] U.S. Cl. ...................................... 433/90; 433/164
[58] Field of Search ...................... 433/83, 89, 90, 164

[56] References Cited

U.S. PATENT DOCUMENTS

| 833,044 | 10/1906 | Goodhugh. | |
|---|---|---|---|
| 1,676,715 | 7/1928 | Snyder | 433/164 |
| 1,797,866 | 3/1931 | Ivory | 433/83 |
| 2,349,607 | 5/1944 | Berger | 32/17 |
| 2,603,871 | 7/1952 | Call | 433/164 |
| 2,681,408 | 6/1954 | Bronk | 219/39 |
| 2,696,670 | 12/1954 | Thurman | 32/60 |
| 2,958,947 | 11/1960 | Clayton | 433/90 |
| 3,721,006 | 3/1973 | Malmin | 32/40 R |
| 3,855,702 | 12/1974 | Malmin | 32/15 |

OTHER PUBLICATIONS

Hu-Friedy Catalog (p. 13) "Leadership Through Quality".
Misdom-Frank Corporation Catalog (p. 87); 1977 Catalog; published by Misdom-Frank Corporation, New York, New York, 1966.
S. S. White Pennwalt Instruments Catalog for 1977 (p. 8).
Premier Dental Products Co., Norristown, PA. 19401 Catalog (p. 81).

Primary Examiner—Gene Mancene
Assistant Examiner—David I. Tarnoff
Attorney, Agent, or Firm—Price, Heneveld, Huizenga & Cooper

[57] ABSTRACT

The specification discloses an amalgam carrier for pushing amalgams into previously difficultly accessed tooth cavities such as in distal and lingual surfaces. The carrier includes an elongated handle, a support arm extending laterally of the handle, and a release mechanism mounted on the support arm and defining an amalgam bore opening away from the support arm in a direction generally common with the handle. The release mechanism is actuable in the vicinity of the support arm whereby the carrier can be firmly grasped about said handle and the release mechanism actuated by the user's thumb. Also disclosed is a method of pushing an amalgam utilizing the amalgam carrier of the present invention.

10 Claims, 3 Drawing Figures

U.S. Patent      May 7, 1985      4,515,563
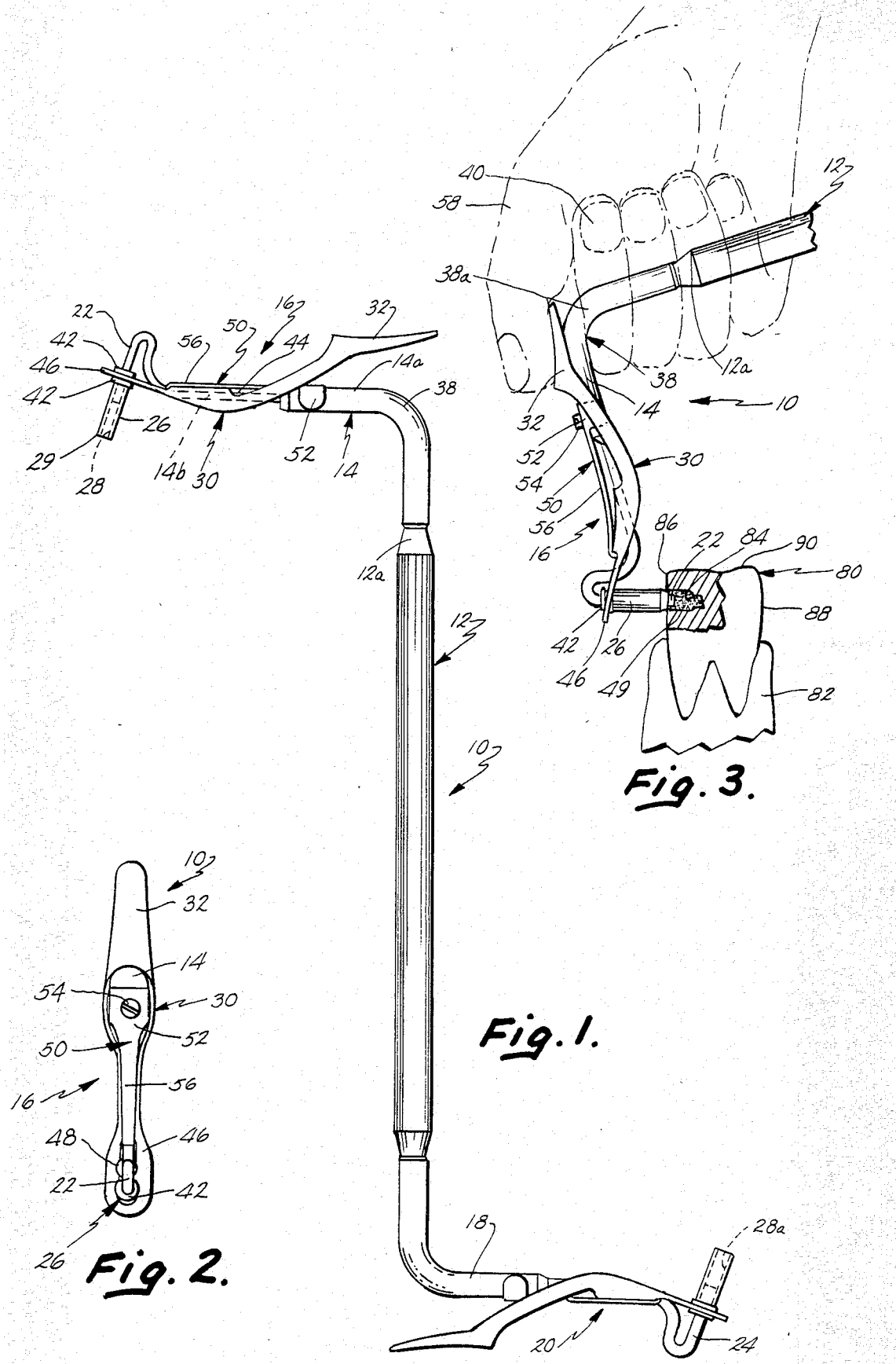

AMALGAM CARRIER

BACKGROUND OF THE INVENTION

The present invention relates to dental instruments, and more particularly to amalgam carriers.

To properly fill a tooth, a dentist must carefully first form the tooth cavity by drilling the tooth to remove all decayed material. A sterilized amalgam must then be mixed and inserted into an amalgam carrier. The tooth cavity must be sterilized and the amalgam pushed into the cavity using the amalgam carrier. Excess amalgam extending from the cavity to or below the gum line is referred to as overhang and must be carefully removed with an amalgam knife or peridontia problems will develop. Although a wide variety of amalgam carriers have been developed to hold the sterilized amalgam and push the amalgam into the tooth cavity, known amalgam carriers are not without their drawbacks.

A "lever-type" amalgam carrier comprises a handle, a generally linear support arm extending from and coaxial with the handle, and a release mechanism mounted on the support arm. The release mechanism defines an amalgam-receiving bore oriented generally perpendicularly to the handle member, a plunger for forcing amalgam out of the bore, and a spring-loaded lever for moving the plunger and amalgam bore relative one another. An example of such a carrier can be seen in U.S. Pat. No. 1,797,866 entitled AMALGAM CARRIER and issued Mar. 24, 1931, to Ivory. Although providing proper amalgam placement in buccal and mesial surfaces, namely those tooth surfaces facing the cheeks and mouth centerline, and crown surfaces, lever-type carriers are extremely difficult or impossible to use when inserting an amalgam in distal and lingual surfaces, namely those surfaces opposite the mesial and buccal surfaces, respectively. Because the amalgam-receiving bore is oriented generally perpendicularly to the handle and because the dentist must work through the relatively restricted opening of a patient's mouth, axially aligning the amalgam bore with a distal or lingual surface tooth cavity is extremely difficult, and consequently the amalgam cannot be properly pushed into the tooth cavity, resulting in an inadequate filling. Occasionally, the amalgam is dropped during an attempt to insert it into a lingual surface, thereby contaminating the amalgam. This results in excessive delay when the contaminated amalgam is scrapped and a new sterilized amalgam prepared. Infrequently, a dentist will simply use the contaminated amalgam without resterilization, resulting in possible serious infection.

A second amalgam carrier is known as a "gun-type" and includes an amalgam-receiving bore, a plunger for expelling an amalgam load from the bore, and an elongated actuating mechanism for interconnecting the bore plunger with an actuating member. An example of this type of carrier can be seen in U.S. Pat. No. 2,696,670 entitled COMBINATION AMALGAM CARRIER AND PLUGGER and issued Dec. 14, 1954, to Thurman. However, because the handle and actuating member are located remotely from the amalgam-receiving bore, accurate positioning of the amalgam load with respect to the tooth cavity is difficult. Accordingly, the problems with amalgam placement and dropping discussed above are also incurred with the gun-type carrier.

SUMMARY OF THE INVENTION

The aforementioned problems are solved by the present invention wherein an amalgam carrier is provided enabling accurate, rapid, and easy placement of an amalgam load in distal and lingual surface cavity. More specifically, the present carrier includes an elongated handle, a support arm extending laterally from the handle, and a release mechanism mounted on the support arm. The release mechanism defines an amalgam-receiving bore extending away from the support arm in a direction generally common with the handle. The release mechanism is actuable in the immediate proximity of the support arm whereby the handle member can be grasped with the fingers of one's hand while the release mechanism can be operated with the thumb.

The present amalgam carrier permits an amalgam load to be rapidly and accurately aligned with and pushed into a distal or lingual surface cavity. The amalgam bore, support arm, and handle together define a generally U-shaped configuration extending behind a tooth when inserted into the patient's mouth. The location of the release mechanism on the support arm enables the carrier to be grasped proximate the amalgam bore to facilitate steady and accurate positioning thereof with the tooth cavity and enables the release mechanism to be actuated when grasping the carrier in this manner. The proper alignment of the amalgam bore with the distal or lingual tooth cavity facilitates accurate amalgam placement, saving time, improving filling quality, and reducing the risk of infection. Overhang problems are virtually eliminated because the amalgam is inserted into the cavity at the proper angle. Therefore, dental patients are provided with fillings of improved quality and sanitation, greatly improving patient comfort and safety.

These and other objects, advantages, and features of the invention will be more readily understood and appreciated by reference to the drawings and specification.

BRIEF DESCRIPTION OF THE DRAWINGS

FIG. 1 is a plan view of the amalgam carrier of the present invention;

FIG. 2 is an end view of the upper release mechanism of the amalgam carrier; and FIG. 3 is a plan view showing the amalgam carrier being utilized to insert an amalgam load into a lingual surface cavity.

DETAILED DESCRIPTION OF THE PREFERRED EMBODIMENT

A double end (DE) amalgam carrier constructed in accordance with a preferred embodiment of the invention is illustrated in the drawings and generally designated 10. Basically, the amalgam carrier comprises elongated handle 12, upper support arm 14, regular tip release mechanism 16, and lower support arm and large tip release mechanism 18 and 20. Support arms 14 and 18 extend generally perpendicularly from handle 12 and terminate in plungers 22 and 24, respectively. Release mechanism 16 includes amalgam load tube 26 defining an amalgam-receiving bore 28 mounted for sliding movement on plunger 22. Further included in release mechanism 16 is lever 30 pivotally supported on support arm 14 to shift amalgam tube 26 relative plunger 22 upon actuation of member 32 between a released position (FIG. 1) and a depressed position (FIG. 3). As seen in FIG. 3, amalgam load tube 26 is easily and accurately aligned with cavity 84 in lingual tooth surface 86. Carrier 10 is grasped about handle 12 at a location generally proximate support arm 14 to facilitate proper positioning and steadying of the carrier during amalgam placement upon depression of lever 32. Consequently, carrier 10 enables the easy, rapid, and accurate placement of an amalgam within a distal or lingual tooth surface.

Turning more specifically to the construction of carrier 10, handle member 12 is a generally linear member having a ribbed or serrated outer surface to facilitate grasping thereof. Upper end 12a of handle 12 is slightly tapered and joined to elbow 38 which interconnects support arm 14 and handle 12. Generally linear arm 14 extends laterally from handle 12 and is oriented generally perpendicularly thereto. Support arm 14 includes handle end 14a joined to elbow 38 and plunger end 14b terminating in plunger 22 oriented at an angle of approximately 80° (i.e., generally peripendicularly) to support arm 14. Elbow 38 is arcuate to provide a comfortable abutment surface for index finger 40 as most clearly seen in FIG. 3.

Amalgam release mechanism 16 is generally well-known in the art and is of the type disclosed in U.S. Pat. No. 1,797,866 cited above. Slide tube 26 defining amalgam bore 28 therein is slidably received on plunger 22 with the plunger fitting closely therein. Slide tube 26 includes an open end 29 opening away from support arm 14 in generally a common direction with handle 12. An annular collar 42 is integral with the slide tube and provides an engagement surface for lever 30, which is pivotally supported on arm 14 to be movable between a released position illustrated in FIG. 1 and a depressed position illustrated in FIG. 3. More particularly, the lever includes a fulcrum portion 44 engaging support arm 14, slide tube end 46, and opposite actuating member 32. Slide tube end 46 defines slot 48 (FIG. 2) within which slide tube collar 46 is received for movement upon actuation of lever 30. Spring 50 includes collar 52, secured about support arm 14 by screw 54, and arm 56 extending from the collar toward plunger 22. Spring arm 56 engages and biases slide tube end 46 toward support arm 14 to urge lever arm 30 and slide tube 26 into their released positions as illustrated in FIG. 1. When actuating member 32 is depressed (FIG. 3), slide tube 26 is drawn upwardly along plunger 22 until the plunger is exposed. Actuating member 32 is generally axially aligned with handle 12 for reciprocable movement in axial alignment therewith.

Release mechanism 20 is generally identical to release mechanism 16 with the exception of the diameters of amalgam load bore 28a and the associated plunger. Suffice it to say that release mechanism 20 provides an amalgam bore 28a of a larger diameter than that of amalgam bore 28 enabling the insertion of a larger amalgam.

OPERATION

Amalgam carrier 10 of the present invention is used to easily, rapidly, and accurately push amalgam load 49 into a lingual surface tooth cavity 84 (FIG. 3). For example, tooth 80 is seated in gum 82 and includes lingual surface 86 facing the tongue (not shown), opposite buccal surface 88, and crown 90. The tooth cavity is first drilled and sterilized in a manner generally well-known to those having ordinary skill in the art. Amalgam load 49 is then prepared and sterilized in a well-known manner and placed into amalgam-receiving bore 28 of slide tube 26 to fill the entire void between plunger 22 and the free end of the slide tube. Carrier 10 is grasped by wrapping the fingers about handle 12 with index finger 40 adjacent or generally proximate elbow 38a and thumb 58 positioned on actuating member 32.

Carrier 10, and more specifically, release mechanism 16 is then inserted into the patient's mouth and slide tube 26 is aligned with cavity 84. The ability to grasp carrier 10 at the action end of the carrier enables the slide tube to be accurately and steadily positioned. When tube 26 is properly oriented, actuating member 32 is depressed by thumb 58 toward handle 12 to expel the amalgam load from slide tube 26 and into cavity 34. The movement of lever member 32 in axial alignment with handle 12 greatly facilitates actuation using thumb 58 while the carrier is grasped as shown. After the load has been fully deposited, the carrier 10 is removed from the patient's mouth and lever 30 is released. The filling is completed by properly condensing the amalgam, for example using a back action plugger, and trimming any excess amalgam with an amalgam knife.

The present amalgam carrier enables the easy, rapid, and most importantly accurate deposite of an amalgam load in a distal or lingual tooth surface. The amalgam load can be accurately and steadily inserted into the cavity, greatly improving the quality of the resultant filling and reducing infection due to contaminated fillings.

The above is intended to be that of a preferred embodiment of the invention. Various changes and alterations might be made without departing from the spirit and broader aspects of the invention as defined in the claims, which are to be interpreted in accordance with the principles of patent law, including the doctrine of equivalents.

The embodiments of the invention in which an exclusive property or privilege is claimed are defined as follows:

1. An amalgam carrier comprising:
   an elongated generally linear handle;
   a support portion extending generally perpendicularly from said handle and terminating in a plunger end, said handle and said support portion connected so as to define an elbow; and
   an amalgam release mechanism supported on said support portion, said release mechanism defining an amalgam bore located at said plunger end, said bore opening away from said support portion in a direction generally common and parallel with said handle whereby said bore can be aligned with a cavity in a distal or lingual tooth surface, said release mechanism including a plunger slidably received within said bore to expel amalgam therefrom and lever means for shifting one of said bore and said plunger relative one another, said lever means including an actuating member generally parallel to said support portion and reciprocable in a direction generally axially aligned with said handle, said actuating member including an actuated position substantially adjacent said elbow wherein said plunger protrudes from said bore to expel amalgam therefrom.

2. An amalgam carrier as defined in claim 1 wherein said elbow interconnecting said handle and said support portion is arcuate to comfortably accommodate one's finger.

3. An amalgam carrier as defined in claim 2 wherein said support portion is generally linear.

4. An amalgam carrier as defined in claim 3 wherein said release mechanism further comprises spring means for biasing said actuating member away from said handle to a released position wherein said plunger is retracted into said bore enabling amalgam to be inserted into said amalgam bore.

5. An amalgam carrier as defined in claim 2 wherein said release mechanism further comprises spring means for biasing said actuating member away from said handle to a released position wherein said plunger is retracted into said bore enabling amalgam to be inserted into said amalgam bore.

6. An amalgam carrier as defined in claim 1 wherein said release mechanism further comprises spring means for biasing said actuating member away from said handle to a released position wherein said plunger is retracted into said bore enabling amalgam to be inserted into said amalgam bore.

7. An amalgam carrier as defined in claim 1 wherein said support portion is generally linear.

8. An amalgam carrier comprising:
   an elongated handle;
   a support arm extending generally perpendicularly from said handle and terminating in an end, said handle and said support arm connected so as to define as elbow; and
   a release mechanism supported on said support arm, said release mechanism defining an amalgam-receiving bore located at said support end and opening away from said support arm in a direction generally common and parallel with said handle, said release mechanism including lever means for expelling amalgam from said bore, said lever means including an actuating member reciprocable in a direction generally axially aligned with said handle between a depressed position substantially adjacent said elbow and a released position, said release mechanism further including means for expelling amalgam from said bore as said actuating member is shifted to said depressed position.

9. An amalgam carrier as defined in claim 8 wherein said elbow interconnecting said handle and said support arm is arcuate to comfortably accommodate one's finger.

10. A method of depositing an amalgam into a distal or lingual surface cavity comprising:
    mounting a lever-type amalgam release mechanism, including an amalgam-receiving bore and an actuating member, generally perpendicularly on a first end of an elongated handle such that the amalgam-receiving bore is disposed laterally of said handle and opens in a direction generally common and parallel with said handle and such that the actuating member is located substantially proximate said first handle end and reciprocates generally axially in line with the handle;
    placing amalgam in said amalgam-receiving bore;
    aligning said bore with a distal or lingual surface cavity; and
    depressing said actuating member to expel the amalgam from the amalgam-receiving bore and into the cavity.

* * * * *

UNITED STATES PATENT AND TRADEMARK OFFICE
CERTIFICATE OF CORRECTION

PATENT NO. : 4,515,563

DATED : May 7, 1985

INVENTOR(S) : Kenneth F. Dungill

It is certified that error appears in the above-identified patent and that said Letters Patent is hereby corrected as shown below:

Column 4, line 23:
"deposite" should be --deposit--; and

Column 5, line 26:
"as" should be --an--.

Signed and Sealed this

Seventeenth Day of December 1985

[SEAL]

Attest:

DONALD J. QUIGG

Attesting Officer

Commissioner of Patents and Trademarks